US00PP09762P

United States Patent [19]

Utecht

[11] Patent Number: Plant 9,762

[45] Date of Patent: Dec. 24, 1996

[54] GERANIUM PLANT NAMED 'FISBRARIS'

[75] Inventor: Angelika Utecht, Montabaur, Germany

[73] Assignee: Florfis AG, Binningen, Switzerland

[21] Appl. No.: 518,893

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisbraris, characterized by its large semi-double flowers having a carmine red color and markings of deeper red color, large, broad umbels, dark-green foliage with weak zonation, compact plant habit, and medium early flower response.

1 Drawing Sheet

The present invention comprises a new and distinct cultivar of geranium, botanically known as *Pelargonium zonale*, and hereinafter referred to by the cultivar name Fisbraris.

Fisbraris is a product of a planned breeding program which had the objective of creating new geranium cultivars with pink flower color, flares on petals, and dark green foliage.

Fisbraris was originated from a hybridization made by inventor Angelika Utecht in a controlled breeding program in Hillscheid, Germany, in 1991. The female parent was the patented cultivar Fisbra, disclosed in U.S. Pat. No. P.P. 8,458, and characterized by single bluish pink flowers and dark green foliage with weak zonation. Fisbra was a mutation of the carmine colored cultivar Fiswig, disclosed in U.S. Pat. No. P.P. 7,385. The male parent of Fisbraris was the patented cultivar Juliet (known also by the tradename "Risque"), disclosed in U.S. Pat. No. P.P. 6,654 and having relatively small pink semi-double florets with darker pink eyes, medium green foliage, well branched plant habit, but late flower response.

Fisbraris was discovered and selected as one flowering plant within the progeny of the stated cross by Angelika Utecht in Spring 1992 in a conrolled environment in Galdar, Gran Canaria, Spain.

The first act of asexual reproduction of Fisbraris was accomplished when vegetative cuttings were taken from the initial selection in June 1992 in a controlled environment in Galdar, Gran Canaria, Spain, by, or under the supervision of, Angelika Utecht.

Horticultural examination of plants grown from these cuttings initiated in May 1993 in Hillscheid, Federal Republic of Germany, and continuing thereafter, have demonstrated that the combination of characteristics as herein disclosed for Fisbraris are firmly fixed and are retained through successive generations of asexual reproduction.

Fisbraris has not been observed under all possible environmental conditions. The phenotpe may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisbraris, which, in combination, distinguish this geranium as a new and distinct cultivar:

1. Large carmine semi-double flowers.
2. Upper and lower petals have darker red markings.
3. Dark green foliage with slight zonation.
4. Compact growth.

5. Medium early flower response.

Of the many commercial cultivars known to the present inventor, the most similar in comparison to Fisbraris are the grandparent cultivar Fiswig and the cultivars Polka (U.S. Pat. No. P.P. 5,371) and Fispol (U.S. Pat. No. P.P. 7,499).

In general comparison to Fiswig, Fisbraris has similar foliage color, but the flower form of Fisbraris is semi-double and the petals are marked with red eyes. In comparision to Polka and Fispol, Fisbraris has darker green foliage and the distinctness of its zonation is intermediate that of Polka and Fispol. Further, Fisbraris has distinct red markings (eyes) on its upper and lower petals, a characteristic lacking in both Polka and Fispol.

The accompanying photographic drawing is a top perspective view and shows typical flower and foliage characteristics of Fisbraris, with colors being as true as possible with illustrations of this type.

In the following description, color references are made to The Royal Horticultural Society Colour Chart.

The color values were determined indoors from flowers taken from plants grown in a greenhouse in May 1994 in Hillscheid, Federal Republic of Germany.

Classification:

*Botanical.*—A hybrid of the species *Pelargonium zonale* l'Hert.

*Commercial.*—Zonal geranium, cv., Fisbraris.

INFLORESCENCE

Umbel:

*Shape.*—Umbrella-shaped or flat semi-spherical.
*Average diameter.*—135 mm.
*Average depth.*—60 mm.
*Peduncle length.*—115 mm.
*Peduncle color.*—Medium green.
*Pedicel length.*—31 mm.
*Pedicel color.*—Green, upper part dark red.
*Number of flowers per umbel.*—20.

Corolla:

*Average diameter.*—47 mm.
*Form.*—Semi-double.
*Number of petals.*—10–12.
*Number of petaloids.*—2–3.
*Color (general tonality from a distance of three meters).*—Carmine red, sometimes with a slight bluish hue.
*Color of upper surface of petals.*—52A.
*Color of lower surface of petals.*—52A-B.
*Markings on petals.*—Red eyes, 46B.

*Color of sepals.*—Green, dark red at base.
*Number of sepals.*—5.

Bud:

*Shape.*—Broad elliptical to round.
*Color (adaxial).*—Light green, red at the base.
*Color (abaxial).*—Rose red to carmine.

Reproductive organs:

*Androecium.*—3–5 fertile anthers, white filaments, yellow-orange pollen.
*Gynoecium.*—5–6 lobed stigma, red style and stigma.
*Seed.*—No seed set observed.

Spring flowering response period: In Hillscheid, Germany, in 1994 plants had on average 0.7 umbels with at least one flower opened 11 weeks after planting of unrooted cuttings.

Outdoor flower production: The flower count in 1994 in Hillscheid, Germany, indicated between 30 and 35 umbels per plant for May through August observation period.

Durability: Good shatter resistance.

PLANT

Foliage:

*Form.*—Kidney-shaped.
*Margin.*—Bicrenated.
*Size of leaf.*—90 mm.
*Color of upper surface.*—Dark green, approximately 137A.
*Color of zonation.*—Darker green, near 139A.
*Tolerance of botrytis.*—Average.

General appearance and form:

*Internode length.*—10 mm.
*Branching pattern.*—1.5 branches per week.
*Length of plants.*—23 cm, (in June, 16-week-old plants).
*Ploidy.*—Tetraploid.

It is claimed:

1. A new and distinct cultivar of geranium plant named Fisbraris, as illustrated and described.

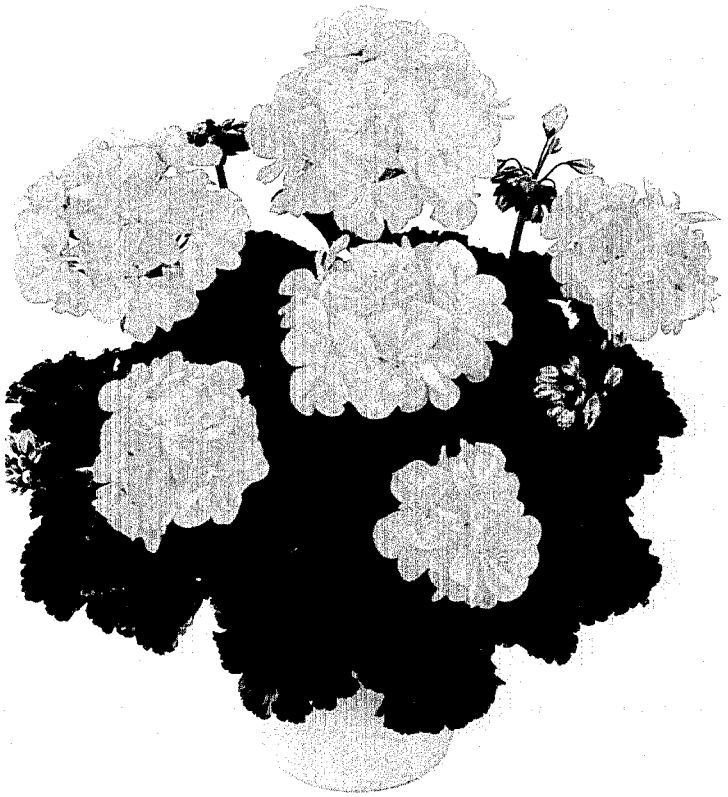

* * * * *